United States Patent
Ni et al.

(10) Patent No.: US 10,212,953 B2
(45) Date of Patent: Feb. 26, 2019

(54) APPARATUS AND METHOD FOR TEMPERATURE CONTROLLED PROCESSES

(71) Applicant: NITECH SOLUTIONS LIMITED, Glasgow (GB)

(72) Inventors: Xiongwei Ni, Edinburgh (GB); Ian Laird, Glasgow (GB); An-Ting Liao, Edinburgh (GB)

(73) Assignee: NITECH SOLUTIONS LIMITED, East Kilbride, Glasgow (GB)

( * ) Notice: Subject to any disclaimer, the term of this patent is extended or adjusted under 35 U.S.C. 154(b) by 866 days.

(21) Appl. No.: 14/805,677

(22) Filed: Jul. 22, 2015

(65) Prior Publication Data

US 2015/0320088 A1 Nov. 12, 2015

Related U.S. Application Data

(62) Division of application No. 12/092,192, filed as application No. PCT/GB2006/004347 on Nov. 22, 2006, now Pat. No. 9,101,901.

(30) Foreign Application Priority Data

Nov. 22, 2005 (GB) .................................. 0523707.8

(51) Int. Cl.
| | |
|---|---|
| *B01D 9/00* | (2006.01) |
| *A23G 1/00* | (2006.01) |
| *A23C 1/00* | (2006.01) |
| *A23L 3/00* | (2006.01) |
| *A23L 3/22* | (2006.01) |
| *B01J 19/00* | (2006.01) |

(Continued)

(52) U.S. Cl.
CPC .............. *A23G 1/0006* (2013.01); *A23C 1/00* (2013.01); *A23L 3/003* (2013.01); *A23L 3/22* (2013.01); *A23L 5/51* (2016.08); *B01D 9/0013* (2013.01); *B01D 9/0036* (2013.01); *B01J 19/006* (2013.01); *B01J 19/0013* (2013.01); *B01J 19/242* (2013.01); *B01J 19/2405* (2013.01); *B01J 19/2425* (2013.01); *C07B 57/00* (2013.01); *F28D 7/14* (2013.01); *F28F 1/40* (2013.01); *F28F 13/10* (2013.01); *F28F 27/00* (2013.01); *A23V 2002/00* (2013.01); *B01J 2219/0006* (2013.01); *B01J 2219/00029* (2013.01); *B01J 2219/0077* (2013.01);

(Continued)

(58) Field of Classification Search
CPC combination set(s) only.
See application file for complete search history.

(56) References Cited

U.S. PATENT DOCUMENTS

| | | | |
|---|---|---|---|
| 1,989,927 | A | 2/1935 | Houdry |
| 3,482,778 | A | 12/1969 | Lanzoni |

(Continued)

FOREIGN PATENT DOCUMENTS

| | | |
|---|---|---|
| EP | 0 096 201 A1 | 12/1983 |
| EP | 0 540 180 A1 | 5/1993 |

(Continued)

*Primary Examiner* — Erin F Bergner
(74) *Attorney, Agent, or Firm* — Nixon & Vanderhye P.C.

(57) ABSTRACT

Method and apparatus for temperature controlled processes in a vessel to provide improved process control, in particular to enable controlled temperatures to be applied to a substance in different process zones of a vessel, has a series of tubular members arranged and operatively connected in a flow system, and each process zone has temperature regulating means juxtaposed thereto for effecting temperature control therein.

17 Claims, 5 Drawing Sheets

(51) Int. Cl.
*B01J 19/24* (2006.01)
*C07B 57/00* (2006.01)
*F28D 7/14* (2006.01)
*F28F 1/40* (2006.01)
*F28F 27/00* (2006.01)
*A23L 5/00* (2016.01)
*F28F 13/10* (2006.01)
*F28D 21/00* (2006.01)

(52) U.S. Cl.
CPC ........ *B01J 2219/00094* (2013.01); *B01J 2219/00155* (2013.01); *B01J 2219/00159* (2013.01); *B01J 2219/00768* (2013.01); *B01J 2219/00777* (2013.01); *B01J 2219/1943* (2013.01); *F28D 2021/0077* (2013.01)

(56) References Cited

U.S. PATENT DOCUMENTS

| | | | |
|---|---|---|---|
| 3,498,061 | A | 3/1970 | Prucha et al. |
| 3,565,784 | A | 2/1971 | Schlinger et al. |
| 3,674,740 | A | 7/1972 | Vernaleken et al. |
| 3,732,110 | A | 5/1973 | Pontecorvo |
| 4,110,521 | A | 8/1978 | Barnett et al. |
| 4,209,599 | A | 6/1980 | Brady et al. |
| 5,977,251 | A | 11/1999 | Kao et al. |
| 6,179,912 | B1 | 1/2001 | Barbera-Guillem et al. |
| 2004/0028582 | A1 | 2/2004 | Carpenter et al. |

FOREIGN PATENT DOCUMENTS

| | | |
|---|---|---|
| GB | 1 206 040 | 9/1970 |
| WO | 99/55457 | 11/1999 |

APPARATUS AND METHOD FOR TEMPERATURE CONTROLLED PROCESSES

This application is a divisional of prior U.S. application Ser. No. 12/092,192, filed Oct. 8, 2008, which was itself a U.S. National Stage of International Application No. PCT/GB2006/004347, filed Nov. 22, 2006 (published on May 31, 2007 as Publication No. WO 2007/060412 A1 in the English language), and which claimed priority to Great Britain Application No. GB 0523707.8, filed on Nov. 22, 2005. The entire disclosure of the prior applications is considered as being part of the disclosure of the present application and is incorporated by reference herein.

The present invention relates to an apparatus and method for controlling a process, especially offering controlled and consistent temperature regulation.

Temperature control is critical in many processes in various fields, including fine and speciality chemicals, pharmaceuticals, bulk chemicals and the food industries. In particular, many processes rely on the maintenance of a constant temperature, or a controlled incremental increase or decrease in temperature. The maintenance and control of temperature becomes particularly important, and often problematic, when carrying out reactions and processes on a large commercial scale.

Traditionally, large scale chemical reactions are carried out in batch processes. Such processes normally involve the use of a stirred tank reactor, in which the reactants are mixed by means of one or more impellers in fixed positions. However, the degree to which temperature regulation, and in particular cooling or heating, can be controlled in batch reactors is restricted—in many cases, cooling to a final desired temperature can take up to several days.

As it can be difficult to accurately control the temperature of a batch reactor, cooling and heating often occur with inhomogeneity; that is, different areas of the reactor cool or heat at different rates. The rate of temperature change (measured in degrees centigrade per minute (° C./min)) is difficult to keep constant over the whole volume of the tank, and over the whole of the cooling/heating period. As a result, many of the products synthesised in batch reactors have undesirable characteristics. For example, different heating or cooling rates in a reactor lead to different reaction rates, which in turn results in the formation of more side products thereby reducing the selectivity, yield or conversion of a given process. In the case of crystalline products, a temperature gradient within a vessel may produce crystals of different morphologies and different sizes. In addition, it is common for crystallisation products to stick to the walls of batch reactors. A further disadvantage of batch reactors is that they do not offer a convenient, effective or efficient way of separating different types of crystal, for example enantiomers.

Several processes in the food industry also require the accurate and consistent control of temperature. For example, pasteurisation of milk and the manufacture of chocolate require a controlled incremental increase or decrease in temperature over a set period of time. However, the fine control of these conditions can prove problematic, and can restrict the rate at which such processes can be carried out.

Therefore, it is an object of the present invention to overcome at least some of the drawbacks associated with the prior art.

A further object of the invention is to provide a versatile apparatus readily adaptable to a number of differing processes, and a method of use thereof for conducting such processes.

Further aims and objects of the invention will become apparent from reading the following description.

According to a first aspect of the present invention there is provided an apparatus for controlling a process, comprising a vessel adapted to receive and discharge fluids, and having a series of tubular members, each defining a discrete process zone, arranged and operatively connected in a flow system to form at least one continuous fluid flow path having an inlet and an outlet, wherein mixing means is provided within the flow path, and wherein each zone has temperature regulating means juxtaposed thereto for effecting temperature control therein.

Preferably the temperature regulating means comprises global temperature regulating means.

Preferably the tubular member and the temperature regulating means are substantially co-axial.

Preferably the global temperature regulating means is a shell that covers the tubular member.

The internal surface of the shell may comprise at least one fin. The fins can be fixed to the inside of the shell to promote turbulence and enhance the efficiency of cooling and/or heating.

The global temperature regulating means can have a counter-current or co-current flow arrangement.

Preferably the temperature regulating means further comprises local temperature regulating means.

The local temperature regulating means can be operatively connected to the global temperature regulating means, and can comprise a series of branches that extend from a manifold. Furthermore, the branches can be juxtaposed to the tubular members that define the discrete process zones. The temperature of each branch can be independently controlled.

Therefore, the vessel can be set such that the temperature of the contents is different in different process zones or flow paths. This can be done accurately and consistently, giving greater control over the temperature of the contents of the tubular members of the vessel. This is very useful in applications such as crystallisation and distillation where the accurate control of temperature has a significant impact on the end product.

The preferred mixing means comprises at least one baffle, more preferably a plurality thereof.

The, or each, baffle extends inwardly from interior surfaces of the tubular members.

Preferably, said tubular members are cylindrical tubes, and said baffles are provided as plates extending radially inwards towards the centre of the cylindrical tubes.

The baffles may be mounted on rails attached to the inner surfaces of the tubular members. The baffles are preferably orifice baffles.

Preferably the apparatus further comprises at least one supply means to supply a feed of at least one flowable media to the vessel.

Optionally the apparatus further comprises at least one process regulating means. The process regulating means can be operatively connected to the tubular members.

The process regulating means may comprise at least one filter adapted to selectively remove precipitated materials. The process regulating means may comprise means for introducing and extracting media. Such process regulating means may be provided in the plane of the tubular assembly or above or below as necessary.

The progress of the process may be locally controlled in each discrete zone by providing each zone with at least one fluid inlet and/or outlet means for the addition or extraction of fluids.

The media may be gases, vapours, liquids, or particles of a size distribution enabling them to behave as fluids, or be readily introduced and carried into the fluid flow within the tubular members of the vessel.

Preferably the apparatus further comprises at least one port for venting a substantially fluid substance. In use of the aforesaid apparatus the substance can be a mixture of miscible or immiscible fluids; a reaction mixture of a chemical reaction; a dispersion, a suspension, an emulsion or micro-emulsion; or any other suitable material or mixture that has at least some fluid properties.

Preferably the tubular member is configured to follow a succession of return paths in one plane thereby forming a substantially repeating S-pattern or serpentine flowpath.

Optionally the tubular member further comprises at least one manifold adapted to divert the flow of the contents of the tubular member along more than one flowpath.

The tubular members may comprise a plurality of interconnected limbs defining common or alternatively different, possibly divergent, flowpaths by use of, for example, Y-connectors.

The tubular members may be aligned in parallel in one plane, and connected by U-connectors to form a plurality of return paths close enough together to reduce the area or "footprint" required but spaced apart to form a grid pattern assembly.

The apparatus preferably comprises a plurality of tubular members operatively connected and configured to follow a convoluted or serpentine path to confine the apparatus to a relatively compact volume (small footprint).

The tubular members may be alternatively positioned and assembled using C-connectors to provide a substantially S-shaped configuration wherein the tubular members are more compactly assembled, alternately diverging and converging rather than lying in parallel.

The addition of a Y-junction, T-piece, cross-piece or manifold allows the contents of the tubular member to be selectively diverted along more than one flow path. This is useful when it is desirable split the contents of the tubular member into more than one separate moiety, such that these separate moieties can be subject to different types of manipulation. For example, one of the moieties can be seeded to produce an enantiomerically pure compound, whilst the other moiety can be seeded to produce the opposite enantiomer. In another example, one of the moieties is cooled relatively quickly to produce small crystals, whilst the other moiety is cooled relatively slowly to produce larger crystals.

Preferably the apparatus further comprises flow control means operatively connected to the vessel.

Preferably the flow control means effects continuous, or plug flow, of media through the vessel.

The flow control means may be adapted to initiate and maintain uniform mixing and efficient dispersion of at least one fluid in the vessel.

Preferably, the flow control means comprises an oscillator adapted to impart motion to the at least one fluid. The flow control means may be adapted to apply a net flow Reynolds number >100 on the at least one fluid. The motion may be oscillatory motion.

According to a second aspect of the present invention there is provided a method for continuously controlling a process applied to an at least partially fluid media according to a predetermined regime, comprising forming a continuous flow system for fluid media from a plurality of tubular members operatively connected to permit fluid communication therethrough, each tubular member providing a discrete process zone, providing in each tubular member mixing means, providing temperature regulating means juxtaposed to each tubular member, introducing fluid media to the flow system and controlling the temperature regulating means to independently control the temperature of at least one discrete process zone.

The method of the present invention is able to deliver linear or non-linear; consistent or non-consistent temperature changes as a function of time or distance The fluid media can be a mixture of miscible or immiscible fluids; a dispersion, a suspension, an emulsion or micro-emulsion; or any other suitable material or mixture that has at least some fluid properties.

Preferably the temperature is varied in ° C. per meter or ° C. per minute.

Optionally the method comprises the further step of adjusting the temperatures of the discrete process zones of the continuous flow system such that the rate of temperature change of the fluid media is consistent along the tubular members.

Alternatively the method comprises the further step of adjusting the temperatures of the discrete process zones of the continuous flow system such that the rate of temperature change of the fluid media is inconsistent along the tubular members.

Optionally the method comprises the further step of adjusting the temperatures of the discrete process zones of the continuous flow system such that the rate of temperature change of the fluid media is linear along the tubular members.

Alternatively the method comprises the further step of adjusting the temperatures of the discrete process zones of the continuous flow system such that the rate of temperature change of the fluid media is non-linear along the tubular members.

The method may optionally comprise the further step of setting a starting temperature at a first end of the continuous flow system, and a finishing temperature at a second end of the continuous flow system, to predetermined constant values. This can be used to selectively crystallise crystals of a particular morphology.

Optionally the method comprises the further step of adjusting the process conditions by introducing or extracting media as necessary.

Preferably the method comprises the further step of selectively precipitating a solid. The precipitated solid may be crystalline.

Optionally the method comprises the further step of adding crystallisation seeds to promote crystallisation.

The seeds may promote the crystallisation of only one enantiomer from a racemic mixture.

Optionally the method comprises the further step of collecting the crystallised enantiomer using at least one filter.

The method may comprise the further step of crystallising and collecting the opposite enantiomer.

Optionally the crystallisation and collection of the two opposite enantiomers is alternated between the two opposite enantiomers.

Alternatively, the crystallisation and collection of the two opposite enantiomers is simultaneous.

The method may comprise the further step of selectively distilling at least one liquid. The method allows for liquids of different boiling points to be distilled in different discrete process zones.

The method may comprise the further step of diverting the flow of the fluid media along disparate tubular members of the continuous flow system by way of a manifold.

By using a manifold or similar device, for example a Y-junction or T-piece, seeds of opposite enantiomers can be added simultaneously to each flow path respectively so that pure compounds with opposite enantiomers can be produced simultaneously. This cannot be achieved in traditional devices. In addition, or alternatively, one of the flowpaths can be cooled relatively quickly to produce small crystals, whilst the other is cooled relatively slowly to produce larger crystals. This again cannot be achieved in traditional devices.

The process according to this invention permits the temperature to be controlled at selected process zones, and optionally also adjust the process by introducing or extracting media at selected process zones.

The process may be one requiring purely temperature controlled processing of fluids, such as pasteurisation, or may involve an intervention to add materials such as seed crystals in a regulated crystal growth process, or a staged chemical reaction wherein reactants to form an intermediate are brought together under appropriate conditions initially in one zone, and the intermediate may be optionally removed from a subsequent zone or reacted with a further reagent at a subsequent zone to prepare a downstream product as may be appropriate.

The present invention will now be described by way of example only, with reference to the accompanying drawings in which.

Figure 1:
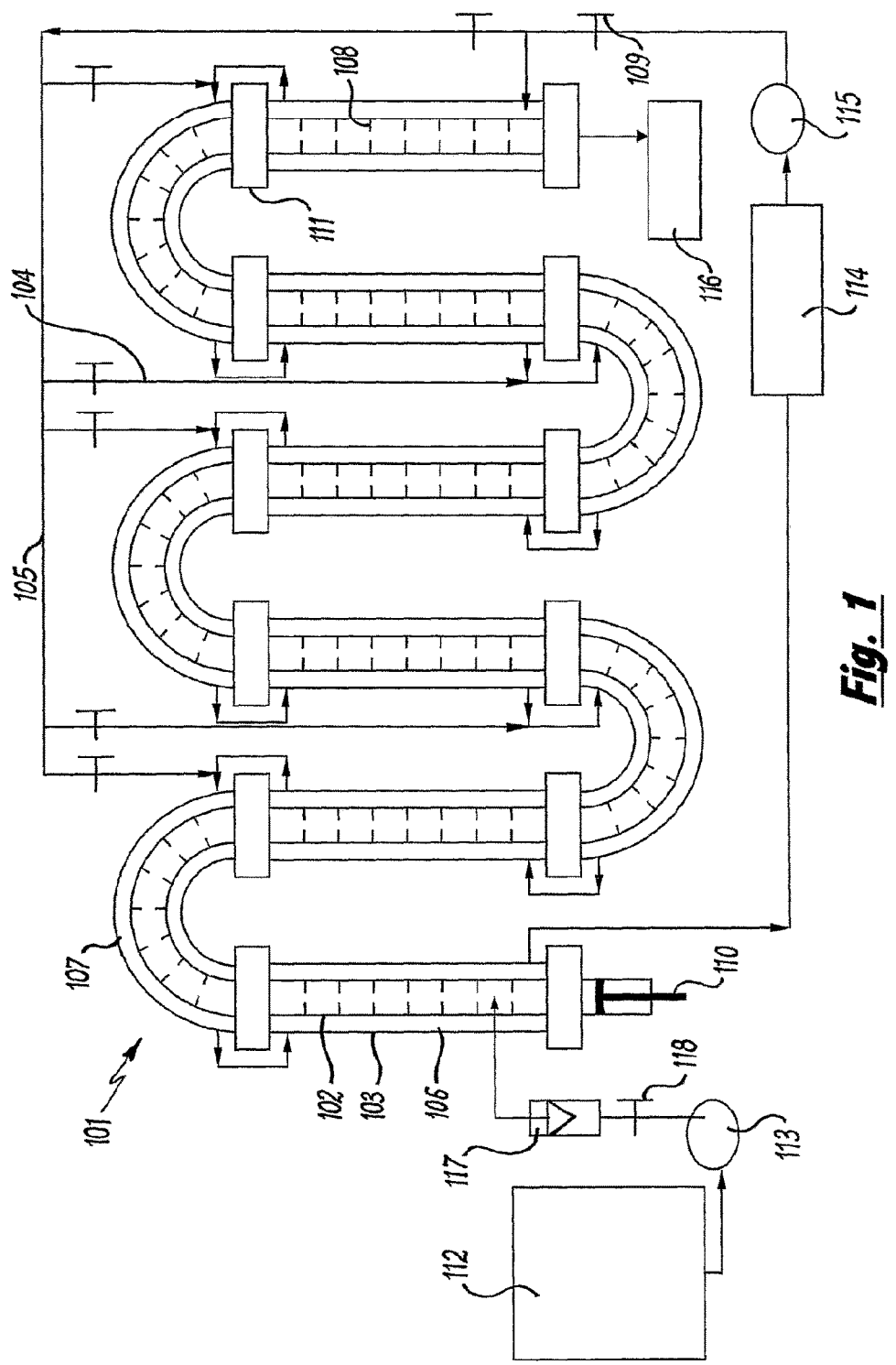
FIG. 1 is a schematic view of a serpentine flowpath oscillatory baffled apparatus suitable for carrying out temperature controlled processes.

Referring now to FIG. 1 there is shown a process apparatus 101 comprising a jacketed vessel 102 encased by a shell 103. The shell 103 contains fluid which acts as global temperature regulation means. The shell 103 has fins (not shown) attached to its internal surface to promote local turbulence in order to enhance the efficiency of cooling or heating. Thermal isolation laggings (not shown) can be applied to the shell 103 to maximise the cooling or heating effect. A series of branches 104 connected to a temperature manifold 105 form a local temperature regulation means. Control valves 109 are placed at points on the local temperature regulation means to divert heating or cooling as the user desires. The arrows superposed on the local temperature regulation means indicate the counter-current direction of flow for a coolant or heating fluid. The local temperature regulation means is equipped with a cooling/heating tank 114 and a pump 115.

The vessel 102 has a plurality of substantially parallel tubular members 106 joined together by U-bends 107 in a serpentine fashion. The vessel 102 contains baffles 108, which are arranged in cells. The number of cells, tubular members and U-bends is not limited. Attached to the vessel 102 at the reactant feed end are a feed tank 112 and a pump 113. Between the pump 113 and the vessel 102 there is positioned a flow meter 117 and an input control valve 118. At the product collection end of the vessel 102 there is connected a centrifugal separator or a collecting tank 116.

The feed tank 112 and pump 113 act as a supply means to supply a feed of at least one flowable media to the vessel 102.

The baffles 108 extend inwardly from interior surfaces of the tubular members 106 which are provided as cylindrical tubes. The baffles 108 are provided as orificed plates extending radially inwards towards the centre of the cylindrical tubes, and mounted on rails (not shown) attached to the inner surfaces of the tubular members 106.

The vessel can be made from separate units, taking the form of individual cells connected by individual U-bends. Alternatively, the vessel can take the form of a single unit, for example a continuous extrusion formed in a desired configuration, or any other structure suitable for forming a continuous flow path. Also, whilst in this example the vessel is, for illustrative purposes, shown as a succession of tubular cells, arranged in parallel and in one plane with return ends (U- or C-bends) to present a serpentine form, it will be understood that it can be of any other convoluted shape, for reasons of compactness, provided that the discrete zones of same are suitable for the application and maintenance of different temperatures. The tubular members can be configured to follow a succession of return paths in one plane.

At one end of the vessel 102 there is a piston 110 to impart oscillatory motion to the contents of the vessel 102. However, other oscillation means can also be used. Control means (not shown) are provided to control both the stroke length and the frequency of oscillation of the piston. The control means is operatively connected to the vessel 102 and is adapted to effect continuous or plug flow of media through the vessel 102. The flow control means can also be adapted to initiate and maintain uniform mixing and efficient dispersion of at least one fluid in the vessel 102, and/or the can be adapted to apply a net flow Reynolds number >100 on at least one fluid.

A number of inlet and outlet ports 111 are situated along the length of the vessel 102, the ports being designed to allow species, seeds or any other additive to be added and/or removed from the tubular member. In addition, the ports provide means for sensing some property of the contents of the tubular member, such as temperature, turbidity and pH. The ports can also provide means for mounting X-ray diffraction (XRD), ultrasonic/Raman spectroscopy (USS) or similar instrumentation along the tubular member to monitor the shape and size of crystals in-situ. The inlet and outlet ports 111 can also be used as process regulating means, operatively connected to the tubular members 106.

In this embodiment a filter or filters can be used in the vessel 102 to selectively remove a substance from inside the vessel 102. For example, when the product of a reaction is crystallised, a particular size distribution, shape or form of crystal can be selectively removed continuously from the vessel 102 using the filters.

The apparatus can have other process regulating means comprising means for introducing and extracting media, such as fluid inlet and/or outlet means for the addition or extraction of fluids or a port for venting a substantially fluid substance.

The temperature regulation along the vessel 102 consists of a global cooling/heating loop in the form of a shell 103 arranged in counter-current fashion in relation to the solution input. The temperature regulation also consists of a local temperature manifold 105 attached to individual branches 104 associated with the individual tubular members 106 of the vessel 102. The local temperature regulation means is connected to the global temperature regulation means in order to enhance local control of temperature.

The temperature manifold, branches and control valves enable the temperature of each branch to be controlled independently from the remaining branches. The branches act as local temperature regulating means and are operatively connected to the shell which acts as global temperature regulating means. Consequently, this apparatus allows the temperature of each tubular member to be independently or collectively controlled.

For example, in a controlled cooling process each branch can be set to an incrementally lower temperature; and in a controlled heating process, each branch can be set to an incrementally higher temperature. In a further alternative, the branches can alternate between increasing and decreasing temperatures.

In the illustrated apparatus for temperature regulation, co-current flows can also be used.

Figure 2:
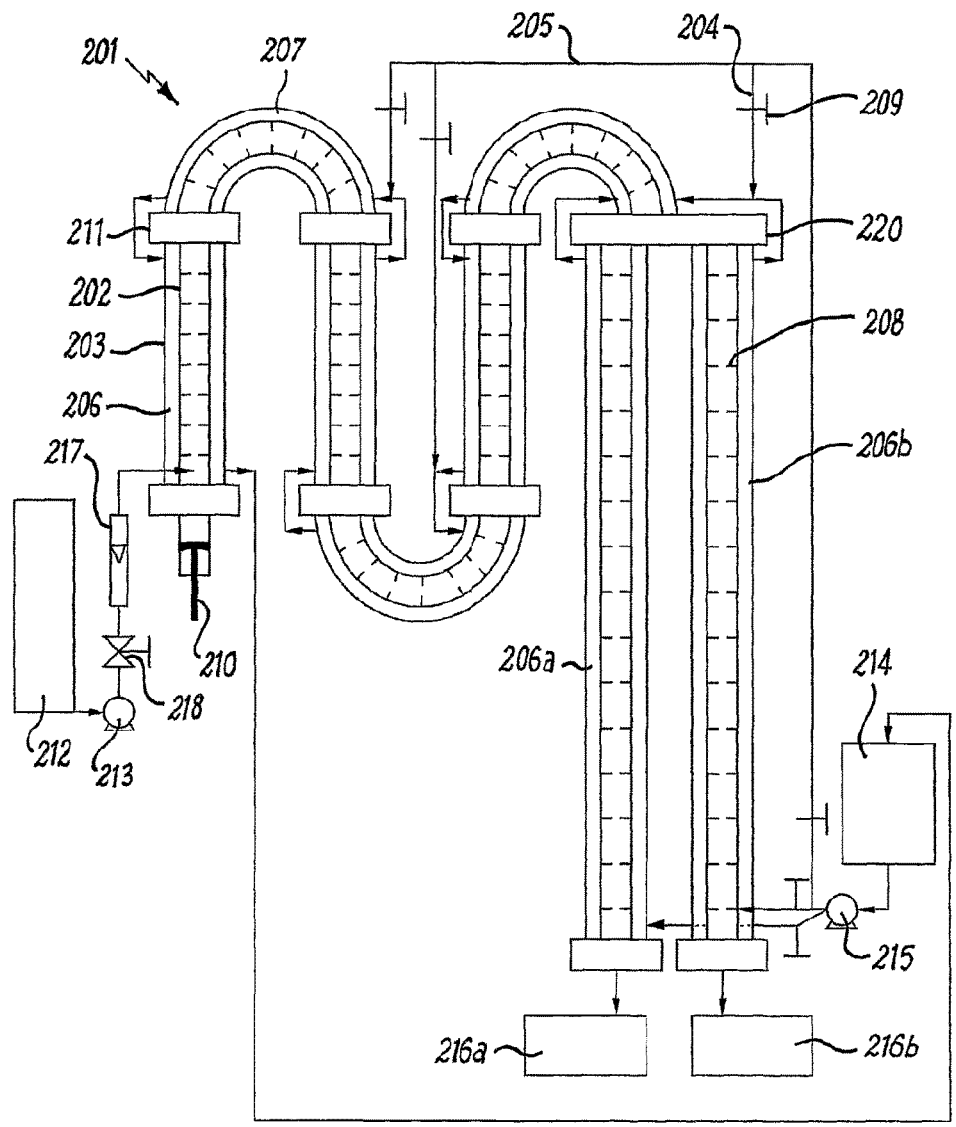
FIG. 2 is a schematic view of an oscillatory baffled apparatus containing a Y-junction, suitable for carrying out temperature controlled processes.

Referring now to FIG. 2, there is shown a process apparatus 201 comprising a jacketed vessel 202 encased by a shell 203. The shell 203 contains fluid which acts as global temperature regulation means. The shell 203 has fins (not shown) attached to its internal surface to promote local turbulence in order to enhance the efficiency of cooling or heating. Thermal isolation laggings (not shown) can be applied to the shell 103 to maximise the cooling or heating effect. A series of branches 204 connected to a temperature manifold 205 form a local temperature regulation means. Control valves 209 are place at points on the local temperature regulation means to divert heating or cooling as the user desires. The arrows superposed on the local temperature regulation means indicate the counter-current direction of flow for a coolant or heating fluid. The local temperature regulation means is equipped with a cooling/heating tank 214 and a pump 215. At one end of the vessel 202 there is a piston 210 to impart oscillatory motion to the contents of the vessel 202.

The vessel 202 has a plurality of substantially parallel tubular members 206 joined together by U-bends 207 in a serpentine fashion. The vessel 202 contains baffles 208, which are arranged in cells. The number of cells, tubular members and U-bends is not limited. Attached to the vessel 202 at the reactant feed end are a feed tank 212 and a pump 213. Between the pump 213 and the vessel 202 there is positioned a flow meter 217 and an input control valve 218. A number of inlet and outlet ports 211 are situated along the length of the vessel 202, the ports being designed to allow species, seeds or any other additive to be added and/or removed from the vessel 202.

At a point in the vessel 202 there is provided a Y-junction 220. After the Y-junction the vessel 202 splits into separate tubular members 206a and 206b. The contents of the two separate tubular members 206a and 206b are separate and can be heated/cooled, added to/subtracted from, or otherwise adjusted probed or treated independently. The product collection end of tubular members 206a and 206b are connected to centrifugal separators 216a and 216b respectively.

Whilst in the example given the vessel is split using a Y-junction or Y-connector, it will be appreciated that many different manifold-type arrangements such as T-pieces, cross-pieces or multiple inlet and/or outlet manifolds can be used. For example, the tubular members can comprise at least one manifold adapted to divert the flow of the contents of the tubular member along more than one flowpath.

The apparatus as described comprises a vessel adapted to receive and discharge fluids, and having a series of tubular members, each defining a discrete process zone, arranged and operatively connected in a flow system to form at least one continuous fluid flow path having an inlet and an outlet, wherein mixing means is provided within the flow path, and wherein each process zone has temperature regulating means juxtaposed thereto for effecting temperature control therein.

With reference again to FIG. 1, in a controlled crystallisation process, a supersaturated solution at a given temperature, say 80° C. from the tank 112 is pumped, via an inlet, into the vessel 102 using a pump 113, flow meter 117 and the input control valve 118. The cooling medium (either water or coolant), at 5° C., is pumped, via a first inlet, into the shell 103 from the cooling/heating tank 114 using a pump 115 and control valves 109, counter-current to the solution flow.

The cooling medium leaves the vessel 102 from the final outlet and returns to the cooling/heating tank 114. By controlling both the global flow rate from the first inlet together with the local flow rates from subsequent inlets, a predetermined temperature decreases, say 10° C. per meter from left to right, can be achieved and maintained. As such, the temperature of the contents of the vessel can be controlled in terms of degrees Centigrade per meter (° C./m), or degrees Centigrade per minute (° C./min). This confers to the user a much greater degree of controllability over the physical and chemical properties of the products obtained from the vessel.

Still referring to FIG. 1, the solution cools as it flows from left to right along the vessel 102, and the product crystallises and is suspended in solution until it comes leaves the vessel via an outlet into a centrifugal separator 116. As the temperature decrease is controlled incrementally, the initial temperature, the final temperature and the rate of cooling are constant for the whole of the crystallisation process. Consequently, the crystallisation product is of consistent size and shape.

The apparatus in this example provides a controlled and consistent cooling of the solution over a manageable time period. As such, the products in the vessel are always under the control of the apparatus operator. In contrast, when a product is cooled in a batch reactor, the process can take many hours or days, and the temperature of the product at different parts of the batch reactor is often variable. Furthermore, the bulk cooling gradient can be inconsistent and, importantly, cannot be directly controlled.

Figure 3:
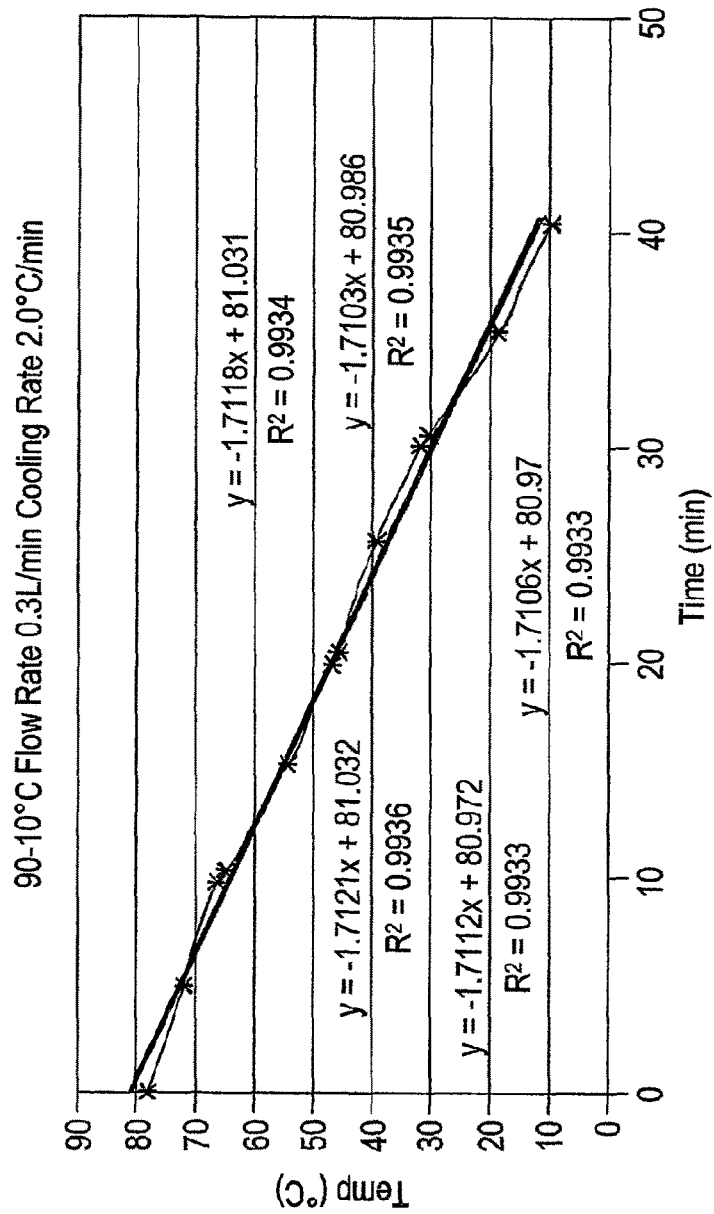
FIG. 3 is a graph that illustrates a linear cooling profile achieved with the present apparatus.

For example, with reference to FIG. 3, there is shown a graph that illustrates a linear cooling profile achieved with the apparatus of the present invention. In this example a solution is cooled from 90° C. to 10° C. at a constant rate of 2° C. per minute to obtain linear cooling over a 40 minute period.

The apparatus facilitates a method for continuously controlling a process applied to an at least partially fluid media according to a predetermined regime. The method as described involves the steps of forming a continuous flow system for fluid media from a plurality of tubular members operatively connected to permit fluid communication therethrough. Each tubular member contains baffles, which act as mixing means when combined with fluid flow or oscillation, and provides a discrete process zone. The apparatus also has branches which provide temperature regulating means juxtaposed to each tubular member. By introducing fluid media to the flow system and controlling the temperature regulating means, it is possible to independently or collectively control the temperature of the discrete process zones.

The temperatures of the discrete process zones of the continuous flow system can be adjusted such that the rate of temperature change of the fluid media is consistent or inconsistent along the tubular members.

The temperatures of the discrete process zones of the continuous flow system can be adjusted such that the rate of temperature change of the fluid media is linear or non-linear along the tubular members.

Various modifications can be made to the method. For example, a fixed starting and finishing temperature can be set to predetermined constant values, and/or the process conditions can be adjusted by introducing or extracting media as necessary.

In the case of crystallisation, crystalline solids can be selectively precipitated by, for example, adding crystallisation seeds. The crystallisation of only one enantiomer from a racemic mixture can be promoted, and collected using a filter. The opposite enantiomer can also be crystallised and collected. The crystallisation and collection of the two opposite enantiomers can be alternated between the two opposite enantiomers, or the crystallisation and collection of the two opposite enantiomers can be simultaneous.

Having accurate control over the temperature of the products in the vessel facilitates selective crystallisation. For example, by carefully selecting different controlled rates of cooling, different sizes of crystal can be precipitated. In addition, by carefully selecting different starting temperatures and different finishing temperatures, crystals with different morphologies can be selectively grown. The filters are used to selectively remove certain sizes or shapes of crystal, whilst allowing the remainder of the solution to progress through the vessel.

Figure 4A:
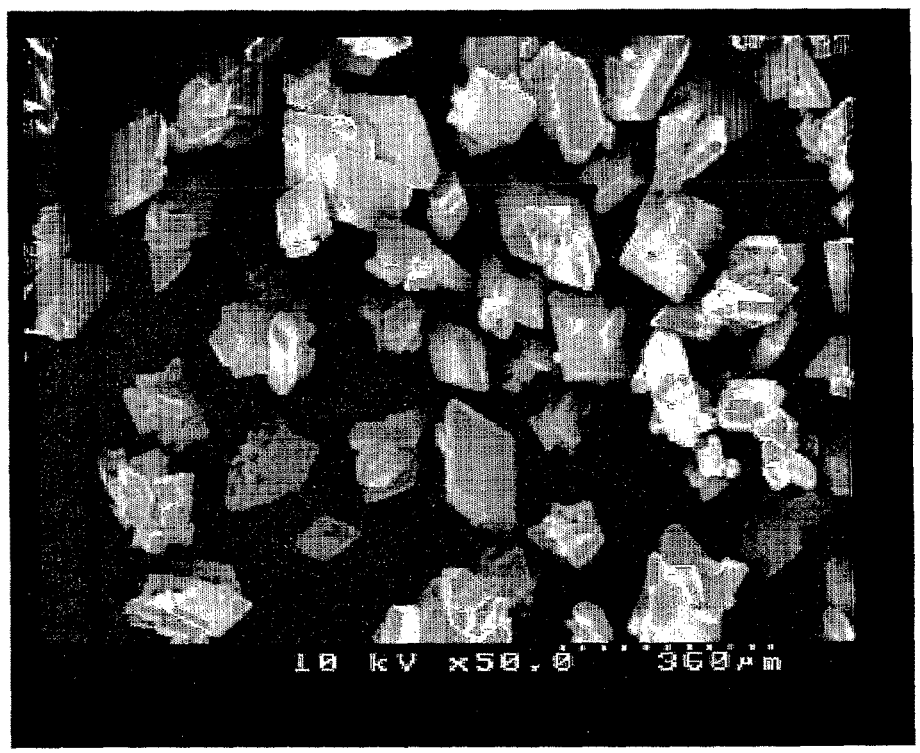
FIGS. 4a and 4b illustrate the different crystal morphologies obtained using different cooling rates.
Figure 4B:
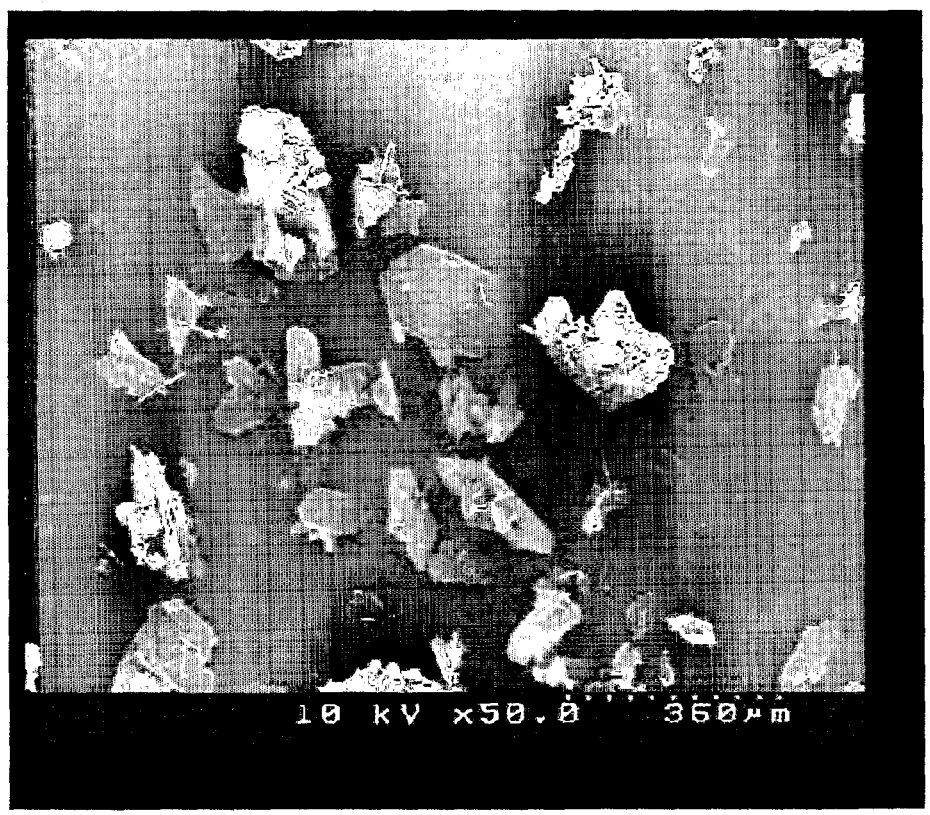

For example, with reference to FIGS. 4a and 4b there is illustrated different crystal morphologies obtained using different cooling rates. FIG. 4a illustrates α-crystals that were obtained using the apparatus of the present invention and a constant cooling rate of 0.6° C. per minute applied from the start of the vessel, for the duration that a reaction mixture is present in a vessel.

In contrast, FIG. 4b illustrates β-crystals obtained using the apparatus of the present invention and a cooling rate of 1.3° C. per minute as applied from half way along the vessel. Therefore, it is clear that the apparatus of the present invention can be used to alter crystal morphology.

The local temperature regulation allows controllable and variable flows (including optionally zero flow) of cooling or heating medium so that the temperature of the individual branches can be different from, or the same as, each other and can be controlled independently or collectively.

Whilst in this example the means for controlling the temperature of the vessel is a jacketed tubular device with both global and local temperature regulation means as described, it will be understood that other suitable means for controlling temperature could be used. Typically such means will be modular in construction which allows the modules to be independently controlled. In this manner, the temperature of discrete zones of the vessel and its contents can be independently controlled.

In an alternative embodiment, individual temperature regulators, not connected by a manifold, can be attached to the limbs of the tubular member. These individually control the temperature of the limbs, and can be set to any desired temperature. Also, the means for regulating temperature can take the form of a heat exchanger, so that the vessel can be submerged in the heat exchanger, thus minimising the loss of energy and making the apparatus more efficient. A further alternative means for regulating temperature is the inclusion of "cold fingers" and/or heating elements inside the tubular members of the vessel. In a still further alternative the baffles can be attached to connecting rods, and this combination can provide means for regulating temperature, by cooling or heating the contents of the vessel.

Use of the apparatus of FIG. 1 will now be described with reference to the pasteurisation of milk.

Prior to the introduction of raw milk, the heating medium (either water or oil), say 85° C. is pumped into the shell 103 surrounding the vessel 102 from the cooling/heating tank 114 via a first inlet, and leaves the shell 103 from a final output, whereon it returns to the cooling/heating tank. The process carries on until all temperature measurements along the vessel 102 show an identical reading. Raw milk from tank 112, at 15° C., is then pumped into the vessel 102 via an inlet. Depending on the required pasteurisation time, the raw milk flows along the vessel 102 from left to right and is pasteurised along the flow path, before it exits the vessel 102, via an outlet, into bottles, cans, cartons, transportation vehicles or storage tanks.

Throughout the process described, the contents of the vessel 102 are mixed by oscillation via the piston 110. In the above example, a constant temperature regulation is required. Should a variable temperature regulation be needed, the local temperature regulation means can be adjusted to provide this.

Use of the apparatus of FIG. 1 will now be described with reference to a distillation process.

Prior to the introduction into the vessel 102 of a mix of liquids with different boiling points, or a liquid containing different fractions of boiling points, a heating medium of oil or steam at approximately 200° C. is pumped into from the heating tank 114 to the shell 103 surrounding the vessel 102. The heating medium is pumped into the shell 103 via a first inlet, and leaves the shell 103 from a final output, whereon it returns to the heating tank 114.

Whilst global heating is applied to the vessel 102, local cooling is applied by reducing the temperature of discrete zones of the tubular members 106, by say 30° C. per predetermined length. In this way, an incremental temperature reduction along the flowpath is achieved. Condensers (not shown) are connected to strategic ports 111 along the length of the vessel 102 to collect different vapour fractions at different points whilst maintaining a continuous flow, thereby achieving continuous distillation.

Referring now to FIG. 2, the vessel 202 forks in the shape of a Y (via a Y-branch 220) in the direction of flow, such that the material flowing through the tubular member 202 may flow along both forks 206a and 206b. In one use of the apparatus, downstream from the Y-branch 220, the contents of the forks 206a and 206b are "seeded" with materials that promote the crystallisation of opposite enantiomers. The opposite enantiomers, which crystallise separately in the two forks 206a and 206b, are then collected simultaneously via centrifugal devices 216a and 216b.

This accurate and selective control of crystal growth, and simultaneous crystal separation, cannot be achieved on any commercial scale in typical batch reactors or the like.

It will also be apparent that the apparatus of present invention can be used such that the rate of cooling or heating, and the initial and final temperatures, can be deliberately deviated to promote the growth of crystals of different sizes and different morphologies.

As described earlier, the crystalline product is of a solid form, hence solids are suspended and transported along the vessel, although the contents of the vessel retain at least some fluid character. The uniform and enhanced mixing, in particular, plug flow characteristics achieved in this type of apparatus, can give rise to effective solid suspensions and effective conveyance of said suspension in the baffled tubular members, with or without oscillation.

Referring once more to FIG. 2, selective distillation can be achieved as follows. A mix of liquids with different boiling points or a liquid containing fractions with different boiling points in the feed tank 212 is pumped through the vessel 202, while the heating medium of oil or steam, at 80° C. is pumped from the heating tank 214 into the shell 203 surrounding the vessel 202. The heating medium is added via a first inlet and leaves the shell 203 from a final output, whereon it returns to the heating tank 214.

The method allows for the selective distillation of at least one liquid, and can afford the diversion of the flow of a fluid media along disparate tubular members of the continuous flow system by way of a manifold.

Once a steady-state is reached, local heating effects are applied to tubular members 106a and 106b such that two different temperature increases are achieved simultaneously thereby affording the selective collection of two different vapours. Such a process cannot be carried out using conventional apparatus.

In all of the above cases, the apparatus used provides for effective and accurate temperature regulation in combination with efficient mixing and dispersion of the vessel contents, to provide and control the type, shape, size and homogeneity of the process being carried out, and of the products that are made. The temperature regulation can be linear, non-linear, or a combination of linear and non-linear.

A process apparatus with more efficient, uniform mixing, plug flow characteristics and much better heat transfer rates avoids the need for scale up and allow crystallisers to be much smaller (by factor of 30-40 fold). This reduces capital costs, space and other overhead requirements and the smaller plant has lower operating costs. Additionally, the plant is skid-mounted and portable.

Improvements and modifications may be incorporated herein without deviating from the scope of the invention.

What is claimed is:

1. A continuously controlled crystallisation process applied to an at least partially fluid media according to a predetermined regime, comprising:
    forming a continuous flow system for fluid media from a plurality of cylindrical tubes operatively connected to permit fluid communication therethrough, each cylindrical tube providing a discrete process zone, the cylindrical tubes being configured to follow a succession of return paths in one plane and being arranged and operatively connected to form at least one continuous fluid flow path having an inlet and an outlet;
    providing in each cylindrical tube a plurality of orificed plates that extend radially inwards towards the center of the cylindrical tubes;
    providing temperature regulating means for effecting independent temperature control over the discrete process zones, the temperature regulating means including a shell that surrounds the cylindrical tubes forming the continuous fluid flow path, a source of a single temperature controlled fluid, a manifold that supplies the temperature controlled fluid, a plurality of branches that extend from the manifold, wherein each branch supplies the temperature controlled fluid to a portion of the shell surrounding each of the discrete process zones, and a plurality of valves, each valve being provided on a branch that extends from the manifold to a portion of the shell surrounding each of the discrete process zones;
    introducing fluid media to the flow system;
    imparting oscillatory motion to the fluid media to initiate and maintain uniform mixing and efficient dispersion thereof;
    controlling the temperature of at least one of the discrete process zones by controlling the flow rate of the temperature controlled fluid through a section of the shell corresponding to the at least one discrete process zone; and
    selectively precipitating a crystalline solid.

2. The process of claim 1, wherein the temperature within the at least one discrete process zone is varied in ° C. per meter.

3. The process of claim 1, wherein the temperature within the at least one discrete process zone is varied in ° C. per minute.

4. The process of claim 1, wherein controlling the temperature of at least one discrete process zone comprises independently controlling the temperatures of a plurality of the discrete process zones by independently controlling flow rates of the temperature controlled fluid through portions of the shell corresponding to the plurality of discrete process zones.

5. The process of claim 4, wherein independently controlling the temperatures of a plurality of the discrete process zones comprises adjusting the temperatures of the plurality of discrete process zones such that the rate of temperature change of the fluid media is substantially consistent along the plurality of discrete process zones.

6. The process of claim 4, wherein independently controlling the temperatures of a plurality of the discrete process zones comprises adjusting the temperatures of the plurality of discrete process zones such that the rate of temperature change of the fluid media is inconsistent along the plurality of discrete process zones.

7. The process of claim 4, wherein independently controlling the temperatures of a plurality of the discrete process zones comprises adjusting the temperatures of the plurality of discrete process zones such that the rate of temperature change of the fluid media is linear along the plurality of discrete process zones.

8. The process of claim 4, wherein independently controlling the temperatures of a plurality of the discrete process zones comprises adjusting the temperatures of the plurality of discrete process zones such that the rate of temperature change of the fluid media is non-linear along the plurality of discrete process zones.

9. The process of claim 1, wherein controlling the temperature further comprises setting a starting temperature at a first end of the continuous flow system and a finishing temperature at a second end of the continuous flow system to predetermined constant values.

10. The process of claim 1, comprising the further step of adjusting the process conditions by introducing or extracting media as necessary.

11. The process of claim 10, comprising the further step of adding crystallization seeds to promote crystallization.

12. The process of claim 11, wherein the crystallization seeds promote the crystallization of only one enantiomer from a racemic mixture.

13. The process of claim 12, comprising the further step of collecting the crystallized enantiomer using at least one filter.

14. The process of claim 13, comprising the further step of crystallizing and collecting the opposite enantiomer.

15. The process of claim 14, wherein the crystallization and collection of the two opposite enantiomers is alternated between the two opposite enantiomers.

16. The process of claim 14, wherein the crystallization and collection of the two opposite enantiomers is simultaneous.

17. The process of claim 13, comprising the further step of diverting the flow of the fluid media along disparate cylindrical tubes of the continuous flow system by way of a manifold.

\* \* \* \* \*